(12) United States Patent
Robertson et al.

(10) Patent No.: US 7,727,309 B2
(45) Date of Patent: Jun. 1, 2010

(54) CARBON DIOXIDE ABSORBENT

(75) Inventors: John Robertson, Stuyvesant Falls, NY (US); Carlos A. Benitez, Asbury Park, NJ (US); Channon Visscher, St. Louis, MO (US); Douglas L. Woerner, Maplewood, MO (US)

(73) Assignee: Allied Healthcare Products, Inc., St. Louis, MO (US)

( * ) Notice: Subject to any disclaimer, the term of this patent is extended or adjusted under 35 U.S.C. 154(b) by 247 days.

(21) Appl. No.: 12/002,449

(22) Filed: Dec. 17, 2007

(65) Prior Publication Data

US 2008/0210091 A1 Sep. 4, 2008

Related U.S. Application Data

(60) Provisional application No. 60/877,218, filed on Dec. 26, 2006, provisional application No. 60/933,032, filed on Jun. 4, 2007.

(51) Int. Cl.
*B01J 20/04* (2006.01)
*B01D 53/62* (2006.01)

(52) U.S. Cl. .................... 95/139; 96/117.5; 252/184

(58) Field of Classification Search .................. 95/139, 95/900; 96/108, 117.5, 118; 502/400; 252/184
See application file for complete search history.

(56) References Cited

U.S. PATENT DOCUMENTS

| | | | | | |
|---|---|---|---|---|---|
| 3,489,693 | A | * | 1/1970 | Bovard | 502/400 |
| 3,607,040 | A | * | 9/1971 | Hervert et al. | 264/109 |
| 3,847,837 | A | * | 11/1974 | Boryta | 502/400 |
| 4,407,723 | A | * | 10/1983 | MacGregor et al. | 252/192 |
| 6,228,150 | B1 | * | 5/2001 | Armstrong et al. | 95/139 |
| 6,867,165 | B2 | * | 3/2005 | Chin | 502/400 |
| 2004/0029730 | A1 | | 2/2004 | Clarke et al. | |
| 2005/0160912 | A1 | * | 7/2005 | Hrycak et al. | 96/243 |

FOREIGN PATENT DOCUMENTS

| | | |
|---|---|---|
| DE | 19740736 | 3/1999 |
| JP | 49-051189 A * | 5/1974 |
| WO | WO/01/45837 | 6/2001 |

* cited by examiner

*Primary Examiner*—Frank M Lawrence
(74) *Attorney, Agent, or Firm*—Linda L. Lewis; Greensfelder, Hemker & Gale, P.C.

(57) ABSTRACT

A carbon dioxide absorbent suitable for use in anesthesiology during low flow or closed circuit made of from 70 to 90% hydrated lime, from 0.1 to 17% of lithium hydroxide or its precursor, or a combination thereof, and from 5 to 25% water, wherein the absorbent provides low Compound A by-product, and high absorbency.

19 Claims, No Drawings

CARBON DIOXIDE ABSORBENT

RELATED INVENTIONS

The present application claims the benefit of provisional applications 60/877,218, filed Dec. 26, 2006, and 60/933,032, filed Jun. 4, 2007.

FIELD OF THE INVENTION

The present invention relates to a carbon dioxide absorbent formulation for gaseous systems, comprising: hydrated lime essentially free of sodium or potassium hydroxides; lithium hydroxide or its precursor; and water. The absorbent formulation is specifically intended for use during low-flow or closed-circuit anesthesia, but may be used for any application in which traditional soda lime absorbents are used.

BACKGROUND OF THE INVENTION

The most common absorbent for carbon dioxide is hydrated lime, or calcium hydroxide. Water is required in the absorbent formulation to serve as a substrate in the net $CO_2$ absorption reaction:

$$CO_2(g) + Ca(OH)_2(s) \rightarrow CaCO_3(s) + H_2O(g,l),$$

in which carbon dioxide reacts with lime to produce calcium carbonate and water. Traditionally, the lime is combined with sodium and/or potassium hydroxide to form soda lime. The presence of strong alkali hydroxides allows soda lime to absorb carbon dioxide more quickly and with greater capacity than mixtures containing only lime and water.

A disadvantage of soda lime is the sensitivity of anesthetic agents to strong hydroxide bases. The most commonly used modern anesthetic agents are fluorinated hydrocarbons, which may chemically react with sodium and/or potassium hydroxide to form potentially toxic by-products. For example, the anesthetic sevoflurane (1,1,1,3,3,3-hexafluoro-2-(fluoromethoxy)propane) has been found to undergo hydroxide-induced dehydrofluorination to produce a fluoro-olefin byproduct called "Compound A" (fluoromethyl-2,2-difluoro-1-(trifluoromethyl)vinyl ether), which is nephrotoxic to rats at concentrations of 60 to 100 ppm and lethal at concentrations of 350 to 400 ppm.

An additional concern when using absorbents containing sodium and/or potassium hydroxides is the possibility of desiccation of the mixture. Highly exothermic chemical reactions between anesthetic agents and dry soda lime release formaldehyde, methanol, and carbon monoxide, which are undesirable by-products. In extreme cases, the heat liberated by these chemical reactions causes a fire.

Two main approaches have been taken to address the problem of by-product Compound A formation and exothermic degradation to formaldehyde, methanol, and carbon monoxide. The first approach is to remove strong alkali hydroxides, such as sodium and potassium hydroxide, from the absorbent formulation. U.S. Pat. No. 6,228,150 and U.S. Pub. No. 2004/0029730 each disclose a carbon dioxide absorbent comprising calcium hydroxide essentially free of sodium and potassium hydroxide. World publication WO 01/45837 discloses a carbon dioxide absorbent comprising lime essentially free of sodium hydroxide, essentially free of water, essentially free of a humectant, and containing at least 20% anhydrous lithium hydroxide. German patent publication DE 197 40 736 discloses the use of lime free of sodium hydroxide and potassium hydroxide, to which barium hydroxide and/or magnesium hydroxide and/or lithium hydroxide may be added. No ranges are disclosed in DE 197 40 736, nor is the water content of the formulation. None of the publications listed above disclose the use of 0.1 to 17% lithium hydroxide, any of its precursors, or any combination thereof, with 70 to 90 wt % hydrated lime and 5 to 25 wt % water.

The second approach used to circumvent anesthetic degradation is the addition of a hygroscopic salt or other humectant to enhance the water retention and/or color indicating properties of the absorbent mixture. Canadian patent 1151633 discloses the use of calcium chloride to enhance the water retention properties of soda lime. U.S. Pub. No. 2004/0029730 discloses the use of 0.2 to 2.0 wt % calcium chloride and/or magnesium chloride in a soda lime absorbent formulation. U.S. Pat. No. 6,228,150 discloses a lime-based carbon dioxide formulation which includes an inorganic humectant, wherein the humectant is calcium chloride hexahydrate and/or magnesium chloride hexahydrate, present in an amount sufficient to yield 7.5 to 20 wt % water. In addition, this publication discloses the addition of 2.5 to 25 vol % of glycerol as an organic humectant. Glycerol is also known to be reactive toward olefin products such as Compound A (Cunningham et al. 1996). U.S. Pat. No. 6,867,165 discloses a carbon dioxide absorbent comprising calcium hydroxide, which may contain sodium or potassium hydroxide, water, a rheology modifier taken from a group of phosphonic acids and salts, and 0.1 to 6.0 wt % calcium chloride to improve color indication properties. None of the publications listed above disclose the use of calcium chloride or any other humectant in a formulation comprising 0.1 to 17 wt % lithium hydroxide or any of its precursors, or any combination thereof, with 70 to 90 wt % hydrated lime and 5 to 25 wt % water.

SUMMARY OF THE INVENTION

The present invention is an absorbent for carbon dioxide comprising: 70 to 90 wt % lime, essentially free of potassium hydroxide and sodium hydroxide; 0.1 to 17 wt % lithium hydroxide, one or more of its precursors, or any combination thereof; and 5 to 25 wt % water. Lithium hydroxide precursors are compounds which will release lithium ions in solution. In the presence of hydrated lime (calcium hydroxide) and water, the lithium-bearing compound will release lithium ions along with calcium ions and hydroxide ions, thereby forming in situ, LiOH. Some examples of LiOH precursors include, but are not limited to, anhydrous lithium hydroxide (LiOH), lithium hydroxide monohydrate (LiOH.$H_2O$), lithium chloride (LiCl), lithium chloride hydrate (LiCl.$H_2O$), lithium carbonate ($Li_2CO_3$), and lithium silicates. In addition, the formulation may include hardening agents, moisture indicators, exhausting indicators, or humectants from about 0.1 to 10 wt. %. The absorbent is granulated and may be used for an application in which soda lime is presently used, such as in submarines, Closed Circuit Underwater Breathing Apparatus, or emergency respiratory apparatus. In particular, the present invention is intended for use in medical anesthesia, including low-flow and closed-circuit anesthesia, because of its compatibility with inhalational anesthetic agents. Because of the increased activity of lithium hydroxide, the life of the absorbent of the present invention is typically longer than that of other commercial products without additional strong alkali.

DETAILED DESCRIPTION OF THE INVENTION

The carbon dioxide absorbent is prepared by mixing the hydrated lime, lithium hydroxide or its precursor, and water to form a paste, which is extruded to form granules. The granulated material is then dried to the desired water content or completely dried and re-hydrated to the desired water content, and screened to retain pellet sizes between about 2 and 5 mm in diameter. Other shapes and sizes of the absorbent of the present invention are also contemplated.

The hydrated lime used in the absorbent is calcium hydroxide essentially free of sodium and/or potassium hydroxide. Minor contaminants may exist in the hydrated lime. Lithium hydroxide precursors are compounds which will release lithium ions in solution. In the presence of hydrated lime (calcium hydroxide) and water, the lithium-bearing compound will release lithium ions along with calcium ions and hydroxide ions, thereby forming in situ, LiOH. Some examples of LiOH precursors include, but are not limited to, anhydrous lithium hydroxide (LiOH), lithium hydroxide monohydrate ($LiOH.H_2O$), lithium chloride (LiCl), lithium chloride hydrate ($LiCl.H_2O$), lithium carbonate ($Li_2CO_3$), and lithium silicates. One or more precursors may be used in combination. The amount of lithium hydroxide in the absorbent formulation is calculated according to the type of precursor or precursors used in its preparation. If anhydrous lithium hydroxide is used in preparation, it is hydrated during processing to give lithium hydroxide monohydrate, which in turn will release lithium and hydroxide ions in the lime and water mixture.

The present invention is further comprised of substances which improve processing and manufacturing properties, or which improve utilization efficacy or anesthetic compatibility. In a preferred embodiment of the invention, from about 0.1 to 5.0% calcium chloride is present as a humectant. The absorbent formulation may further include 0.5 to 5.0% glycerol as a humectant and as a chemical scavenger of the fluoroolefin Compound A.

The formulation of the invention may additionally comprise other minor components including an indicator dye, selected from ethyl violet, methyl violet, Titan yellow, Kenazol yellow, or Clayton yellow, present in the amount of 0.01 to 0.30%. Hardening agents, such as calcium chloride, magnesium chloride, aluminum silicate, lithium silicate, calcium sulfate, or magnesium sulfate may be present in the amount of 0.1 to 10%. From about 0.1 to 5.0% of alkali halides and/or alkaline earth halides can also be added as minor components.

EXAMPLES OF THE INVENTION

Samples of the claimed absorbent formulation containing lithium hydroxide, its precursor, or a combination thereof, were prepared and tested. The following examples of the invention are for purposes of illustration only and are not to limit the claims of the invention in any way. All percentages are by weight unless otherwise indicated.

Example 1

Approximately 92 g lithium silicate aqueous solution (containing 20 wt. % lithium silicate) was mixed in 284 g water, followed by the addition of 31 g of glycerol. The resulting solution was then mixed with 1172 g of hydrated lime. In a separate container, 53 g of lithium hydroxide monohydrate was dissolved in 400 g water, followed by the addition of 15 mL of an aqueous ethyl violet indicator solution. The hydroxide solution was then mixed into the lime-silicate-glycerol mixture to the desired consistency and texture. The resulting paste was extruded to give cylindrical pellets approximately 3 mm in diameter and 3 to 10 mm in length. The pellets were oven dried at 110° C. to the preferred water content of about 15 wt %.

Example 2

Approximately 92 g lithium silicate aqueous solution (containing 20% lithium silicate) was mixed in 284 g water, followed by the addition of 31 g of glycerol. The resulting solution was then added to 1184 g of hydrated lime and mixed to the desired consistency and texture. The resulting paste was extruded into pellets and dried to the desired water content.

Example 3

Approximately 8 g of lithium hydroxide monohydrate was dissolved in 460 g water, followed by the addition of approximately 15 mL of an aqueous ethyl violet indicator solution. The hydroxide solution was then mixed with 1288 g of hydrated lime. In separate container, approximately 34 g of calcium chloride was dissolved in 460 g water. The chloride solution was then added to the lime-hydroxide mixture and mixed; the resulting paste was then extruded into pellets and dried to the desired water content.

Example 4

Approximately 8 g of lithium chloride and 23 g of calcium chloride were dissolved in 920 g water, followed by the addition of approximately 15 mL of an aqueous ethyl violet indicator solution. The chloride solution was then mixed with 1296 of lime; the resulting paste was then extruded into pellets and dried to the desired water content.

After preparation, Examples 1-4 were tested in an anesthesia breathing circuit to measure carbon dioxide absorption performance and to monitor the formation of Compound A or other degradation byproducts. In these experiments, approximately 1 kg of absorbent was placed in the lower (downstream) absorbent canister of an anesthesia machine (North American Drager NARKOMED 2). A tidal volume of 500 mL was used at a breathing rate of 20 breaths per minute for a total volume of 10 liters per minute. The inspiratory:expiratory ratio was 1:2. The sevoflurane concentration was set to 4% by volume (North American Drager Vaporizer 19.1). The fresh gas rate was 1 liter minute (600 mL $N_2O$/400 mL $O_2$) to simulate low-flow anesthesia conditions. A $CO_2$ flow rate of approximately 400 mL per minute was delivered to an artificial lung to achieve 4% $CO_2$ in the expired gas. An ultrasonic bath was included in the lung assembly to achieve 100% relative humidity. Medical capnometers (DATASCOPE Multinex 4000) were used to monitor anesthesia circuit gases (sevoflurane, $N_2O$, $O_2$, $CO_2$) throughout the experiment: inspired gases coming from the absorbent canister (the inspiratory limb), and expired gases coming from the artificial lung (the expiratory limb). Carbon monoxide in the inspiratory limb was measured by sampling capnometer exhaust with a CO monitor (VULCAIN VA301D2). Gas samples were drawn from the inspiratory limb in order to monitor degradation by-products (such as Compound A) by gas chromatography. Each experiment was concluded when $CO_2$ gas concentration climbed to 0.5% by volume in the inspiratory limb of the breathing circuit.

Table 1 summarizes the testing results for Examples 1-4, which comprise lithium hydroxide or one or more of its precursors. The amount of lithium hydroxide precursor or precursors in each formulation is given in weight percent, listed as the anhydrous species. The absorption performance of each sample is measured by its utilization: liters of carbon dioxide absorbed per kilogram of absorbent until exhaustion (0.5% $CO_2$ in the inspiratory limb), as determined by mass gain.

TABLE 1

Examples of the Invention using LiOH Precursors

| Example | Formulation (% as wt % of final product)[1] | Cmpd A (ppm) | CO max (ppm) | Utilization (L/kg) |
|---|---|---|---|---|
| 1 | 2.5% LiOH, 1.5% Li-silicate, 2.5% glycerol | 4 ± 1 | 3 | 166 |
| 2 | 1.5% Li-silicate, 2.5% glycerol | 6 ± 2 | 2 | 164 |
| 3 | 0.3% LiOH, 2.2% $CaCl_2$ | 2 ± 1 | n.d. | 168 |
| 4 | 0.5% LiCl, 1.5% $CaCl_2$ | 2 ± 1 | n.d. | 169 |

[1] The balance of the formulations is lime and water.

The utilization results in Table 1 demonstrate the similar performance of formulations prepared using different LiOH precursors. Samples prepared using lithium hydroxide monohydrate, lithium silicate, and lithium chloride absorb between 164-169 liters of carbon dioxide per kilogram of absorbent under low-flow anesthesia conditions. The addition of calcium chloride in the formulation as a humectant and hardening agent lowered the production of the sevoflurane degradation by-products compound A and carbon monoxide. Examples 3 and 4 were prepared in such a way so as to result in an identical absorbent composition of 0.1% lithium, 1.4% chlorine, 16% water, and 82.5% hydrated lime by weight. The degradation and utilization results in Table 1 further demonstrate the equivalence of using lithium hydroxide monohydrate and/or lithium chloride as precursors to lithium hydroxide in carbon dioxide absorbent formulations.

Examples 5-8

In a preferred embodiment of the invention, the absorbent formulation comprises 70-90 wt % calcium hydroxide; 5-25% water; 0.01-0.3% ethyl violet as an indicator dye; 0.1 to 17% LiCl as a lithium hydroxide precursor; and 0.1 to 5.0% $CaCl_2$ as a humectant. Samples of the preferred formulation were prepared as Examples 5-8, and tested for pellet hardness, the production of sevoflurane degradation by-products, and carbon dioxide utilization. Experimental results for Examples 5-8, comprising LiCl as the lithium hydroxide precursor and $CaCl_2$ as a humectant, are given in Table 2.

TABLE 2

Examples of the Invention using LiCl as Precursor

| Example | Formulation (% as wt % of final product) | Hardness (USP %) | Cmpd A (ppm) | CO max (ppm) | Utilization (L/kg) |
|---|---|---|---|---|---|
| 5 | 0.89% LiCl, 0.14% $CaCl_2$ | 68 | 5 ± 2 | n.d. | 177 |
| 6 | 0.89% LiCl, 1.84% $CaCl_2$ | 88 | 2 ± 1 | n.d. | 159 |
| 7 | 0.18% LiCl, 1.07% $CaCl_2$ | 83 | 4 ± 1 | n.d. | 175 |
| 8 | 0.18% LiCl, 2.77% $CaCl_2$ | 91 | 2 ± 1 | n.d. | 153 |

The results in Table 2 illustrate that the addition of lithium chloride as the lithium hydroxide precursor and calcium chloride as a humectant have the following general effects on absorbent performance: increasing the amount of $CaCl_2$ in the formulation increases pellet hardness, decreases utilization, and lowers Compound A production; whereas increasing the amount of LiCl in the formulation increases the carbon dioxide utilization and decreases pellet hardness. For all examples listed in Table 2, the carbon monoxide concentration in the anesthesia circuit remained below detection levels throughout the experiment.

Comparison of the Invention to Commercial Absorbents

Example 9

In a preferred embodiment of the invention, hereinafter Example 9, the formulation comprises: 0.025% ethyl violet indicator; 0.5% lithium chloride; 2.0% calcium chloride; from 13-18% water; and from 79-84% hydrated lime; prepared as follows. Approximately 8 g of lithium chloride and 32 g of calcium chloride were dissolved in 923 g water, followed by the addition of approximately 15 mL of an aqueous ethyl violet indicator solution. The chloride solution was then mixed with 1288 g of hydrated lime; the resulting paste was then extruded into pellets, dried to the desired water content, and screened to give pellet sizes between about 0.2 and 0.5 cm in diameter.

Multiple samples of Example 9 were compared with commercial carbon dioxide absorbents in tests of absorption capacity and compatibility with anesthetic agents such as sevoflurane. Commercial absorbents included the following formulations shown in Table 3.

TABLE 3

Compositions of Commercial Absorbents and an Example of the Present Invention[1]

| % Component | Absorbent 1 | Absorbent 2 | Absorbent 3 | Absorbent 4 | Example 9 |
|---|---|---|---|---|---|
| KOH | 5.0 | | | | |
| $Ba(OH)_2$ | 10.0 | | | | |
| Silicate | 1.0 | | | | |
| NaOH | | 3.0 | 1.0 | | |
| $CaCl_2$ | | | 2.0 | 3.0 | 2.0 |
| $Ca(SO_4)$ | | | 1.0 | 3.0 | |
| LiCl | | | | | 0.5 |

[1] The balance of the formulations was lime and water.

Both carbon dioxide absorption capacity (utilization) and generation of Compound A were tested using samples of fresh absorbent at the anesthesia conditions described above. Samples of the commercial absorbents and Example 9 were also desiccated to test their compatibility with sevoflurane under dry conditions. For these tests, the absorbent samples were placed in a high flow of oxygen gas until their moisture content was nearly 0 wt %. The dried samples were then exposed to a mixture of 87% oxygen, 8% sevoflurane, and 5% carbon dioxide. Using gas chromatography, the anesthesia circuit gas was tested for methanol and carbon monoxide, products of unwanted side-reactions between sevoflurane and desiccated absorbent. The testing results for each of these experiments are summarized in Table 4, which lists Compound A formation and utilization for fresh absorbent, and methanol and carbon monoxide production for desiccated absorbent.

TABLE 4

Comparison of the Invention to Commercial Absorbents

| | | Fresh absorbent | | Desiccated absorbent | |
|---|---|---|---|---|---|
| Sample | Hardness (USP %) | Cmpd A (ppm) | Utilization (L/kg) | Methanol (ppm) | CO avg (ppm) |
| Absorbent 1 | 68 ± 6 | 58 ± 7 | 148 ± 7 | >500 | >250 |
| Absorbent 2 | 96 ± 2 | 35 ± 6 | 162 ± 8 | 111 ± 25 | 65 ± 13 |
| Absorbent 3 | 94 ± 1 | 3 ± 1 | 134 ± 24 | 1 ± 1 | n.d. |
| Absorbent 4 | 96 ± 1 | 1 ± 1 | 138 ± 13 | n.d. | n.d. |
| Example 9 | 90 ± 3 | 2 ± 1 | 155 ± 24 | n.d. | n.d. |

The results in Table 4 indicate that samples of Example 9 produce much less compound A than samples of traditional absorbents which contain potassium hydroxide (Absorbent 1) or sodium hydroxide (Absorbent 2). The absorbent in Example 9 also has a greater carbon dioxide absorption capacity than commercial absorbents which contain calcium chloride (Absorbents 3 and 4), while maintaining good pellet hardness and minimal compound A production.

Furthermore, traditional absorbents which contain potassium hydroxide (Absorbent 1) or sodium hydroxide (Absorbent 2), when desiccated, react with sevoflurane to generate significant amounts of methanol and carbon monoxide in the anesthesia breathing circuit. Desiccated samples of Example 9 show no such evidence of unwanted side reactions between sevoflurane and the dry absorbent. Taken together, the testing results indicate that the preferred absorbent formulation of the present invention provides: greater absorbance capacity than most commercial absorbents; minimal production of the unwanted fluoro-olefin byproduct Compound A; lowered risk of desiccation from the addition of a humectant; and negligible formation of unwanted byproducts from interactions between desiccated absorbent and sevoflurane.

The invention claimed is:

1. A carbon dioxide absorbent formulation comprising from about 70 to 90 wt. % hydrated lime essentially free of potassium hydroxide and sodium hydroxide; from about 0.1 to 17 wt. % lithium hydroxide or its precursor or a combination thereof; and from about 5 to 25 wt. % water.

2. The absorbent of claim 1, wherein the lithium hydroxide precursor is selected from the group consisting of lithium hydroxide, lithium hydroxide monohydrate, lithium chloride, lithium chloride hydrate, lithium carbonate, and lithium silicate and a combination thereof.

3. The absorbent of claim 2, further comprising a hardening agent from about 0.1 to 10.0 wt. %.

4. The absorbent of claim 3, wherein the hardening agent is selected from the group consisting of calcium chloride, magnesium chloride, calcium sulfate, and lithium silicate, and a combination thereof.

5. The absorbent of claim 1, wherein the absorbent also contains an alkali halide or an alkaline earth halide from about 0.1 to 5.0 wt. %.

6. The absorbent of claim 1, which contains from about 0.1 to 5.0 wt. % calcium chloride.

7. The absorbent of claim 2, which contains from about 0.5 to 5.0 wt. % glycerol.

8. The absorbent of claim 1, wherein the lithium hydroxide precursor is lithium hydroxide and/or lithium chloride from about 0.1 to 17 wt. % and the absorbent contains calcium chloride from about 0.1 to 5.0 wt. %.

9. A method of making a carbon dioxide absorbent comprising mixing from about 70 to 90 wt. % hydrated lime, based on the dried absorbent, essentially free of potassium hydroxide and sodium hydroxide; and from about 0.1 to 17 wt. % lithium hydroxide or its precursor or any combination thereof, based on the dried absorbent, in an aqueous suspension or solution, to form a paste, and drying the paste to form the absorbent, wherein the final moisture content of the absorbent is from about 5 to 25 wt. % water.

10. The method of claim 9, wherein indicating dyes, hardening agents, processing agents, and humectants are added to the absorbent before drying.

11. A method of absorbing carbon dioxide in anesthesia gas comprising contacting the anesthesia gas containing carbon dioxide with a carbon dioxide absorbent formulation comprising from about 70 to 90 wt. % hydrated lime essentially free of potassium hydroxide and sodium hydroxide; from about 0.1 to 17 wt. % lithium hydroxide or its precursor or a combination thereof; and from about 5 to 25 wt. % water, to remove carbon dioxide from the anesthesia gas.

12. The method of claim 11, wherein the anesthesia agent is selected from the group consisting of sevoflurane, desflurane, isoflurane, halothane, and enflurane and a combination thereof.

13. The method of claim 11, wherein the lithium hydroxide precursor comprises at least one selected from the group comprising lithium hydroxide, lithium hydroxide monohydrate, lithium chloride, lithium chloride hydrate, lithium carbonate, and lithium silicate, and a combination thereof.

14. The method of claim 11, wherein the absorbent contains at least one hardening agent selected from the group consisting of calcium chloride, magnesium chloride, calcium sulfate, and lithium silicate.

15. The method of claim 11, wherein the absorbent contains from about 0.1 to 5.0 wt. % of an alkali halide or an alkaline earth halide or a combination thereof.

16. The method of claim 11, wherein the absorbent contains from about 0.1 to 5.0 wt. % calcium chloride.

17. The method of claim 11, wherein the absorbent contains from about 0.5 to 5.0 wt. % glycerol.

18. The method of claim 11, wherein the lithium hydroxide precursor is lithium hydroxide and/or lithium chloride from about 0.1 to 17 wt. %, and the absorbent contains calcium chloride from about 0.1 to 5.0 wt. %.

19. The method of claim 11, wherein the absorbent contains from 0.1 to 3.0 wt. % of indicator dye.

* * * * *